(12) United States Patent
Goodwin (10) Patent No.: US 8,128,630 B2
(45) Date of Patent: *Mar. 6, 2012

(54) TIBIAL AUGMENTATION GUIDE

(75) Inventor: Milton Randall Goodwin, Little Rock, AR (US)

(73) Assignee: Howmedica Osteonics Corp., Mahwah, NJ (US)

( * ) Notice: Subject to any disclaimer, the term of this patent is extended or adjusted under 35 U.S.C. 154(b) by 235 days.

This patent is subject to a terminal disclaimer.

(21) Appl. No.: 12/559,860

(22) Filed: Sep. 15, 2009

(65) Prior Publication Data

US 2010/0004702 A1 Jan. 7, 2010

Related U.S. Application Data

(63) Continuation of application No. 11/268,087, filed on Nov. 7, 2005, now Pat. No. 7,618,422.

(51) Int. Cl.
*A61F 2/46* (2006.01)

(52) U.S. Cl. .................. 606/86 R; 606/88

(58) Field of Classification Search .............. 606/87–88, 606/86 R, 79, 80–85, 96–98; 623/20.14–20.34
See application file for complete search history.

(56) References Cited

U.S. PATENT DOCUMENTS

| | | | |
|---|---|---|---|
| 4,000,525 A | 1/1977 | Klawitter et al. | |
| 4,736,737 A | 4/1988 | Fargie et al. | |
| 4,892,093 A | 1/1990 | Zarnowski et al. | |
| 5,053,039 A | 10/1991 | Hofmann et al. | |
| 5,080,675 A | 1/1992 | Lawes et al. | |
| 5,122,142 A * | 6/1992 | Pascaloff | 606/82 |
| 5,122,144 A * | 6/1992 | Bert et al. | 606/88 |
| 5,263,498 A | 11/1993 | Caspari et al. | |
| 5,275,603 A | 1/1994 | Ferrante et al. | |
| 5,364,402 A | 11/1994 | Mumme et al. | |
| 5,395,376 A | 3/1995 | Caspari et al. | |
| 5,403,320 A | 4/1995 | Luman et al. | |
| 5,520,695 A | 5/1996 | Luckman | |
| 5,578,039 A | 11/1996 | Vendrely et al. | |
| 5,624,447 A * | 4/1997 | Myers | 606/96 |
| 5,634,927 A | 6/1997 | Houston et al. | |
| 5,722,978 A | 3/1998 | Jenkins, Jr. | |
| 6,077,270 A | 6/2000 | Katz | |
| 6,602,259 B1 | 8/2003 | Masini | |
| 6,916,324 B2 | 7/2005 | Sanford et al. | |
| 7,104,996 B2 | 9/2006 | Bonutti | |
| 7,285,122 B2 * | 10/2007 | Sanford et al. | 606/87 |
| 2002/0068979 A1 | 6/2002 | Brown et al. | |
| 2003/0216741 A1 | 11/2003 | Sanford et al. | |
| 2004/0049284 A1 | 3/2004 | German et al. | |
| 2004/0107000 A1 | 6/2004 | Felt et al. | |
| 2004/0162619 A1 | 8/2004 | Blaylock et al. | |
| 2005/0143831 A1 | 6/2005 | Justin et al. | |
| 2005/0149042 A1 * | 7/2005 | Metzger | 606/88 |
| 2005/0192588 A1 * | 9/2005 | Garcia | 606/88 |
| 2006/0100714 A1 | 5/2006 | Ensign | |
| 2007/0055269 A1 | 3/2007 | Iannarone et al. | |
| 2008/0275452 A1 * | 11/2008 | Lang et al. | 606/88 |

* cited by examiner

*Primary Examiner* — Eduardo C Robert
*Assistant Examiner* — Jan Christopher Merene
(74) *Attorney, Agent, or Firm* — Lerner, David, Littenberg, Krunholz & Mentlik, LLP (57) ABSTRACT

A guide for use in making tibial augmentation cuts is disclosed. The guide is preferably for use subsequent to an initial cut being made. A method of utilizing the guide, as well as making the initial cut is also disclosed.

20 Claims, 7 Drawing Sheets

TIBIAL AUGMENTATION GUIDE

CROSS-REFERENCE TO RELATED APPLICATION

This application is a continuation of U.S. application Ser. No. 11/268,087, filed on Nov. 7, 2005, the disclosure of which is incorporated herein by reference.

BACKGROUND OF THE INVENTION

The present invention relates to orthopedic cutting blocks or guides and more particularly, to orthopedic cutting blocks or guides for use in making augmentation cuts.

There are currently many different apparatus for use in resecting bone, as well as many different methods of utilizing same. Many of these apparatus are guides or blocks whose purpose is to guide a surgeon in making cuts or resections (e.g.—by utilizing a cutting tool) in a bone. Often times, the ultimate goal in this type of procedure is to provide a bone surface capable of mating with a corresponding surface of an implant or the like. These cutting guides often vary depending upon the type of cutting instruments being used, the bone being resected, or the type of procedure being performed, among other reasons. For example, cutting guides to be used in conjunction with saws or bladed cutting instruments often have slots or grooves formed therethrough and depending upon the specific bone being resected or the implant being implanted, these slots or grooves may be configured and situated differently. Thus, there currently exist many different types of cutting guides in the prior art.

One type of surgery that relies heavily upon the use of cutting guides is surgery involving the knee joint, and its various bone surfaces. During a typical total knee replacement surgery, the surfaces of both the femur and the tibia are resected and fitted with articulating implants in order to restore natural movement of the lower leg with respect to the upper leg. Different cutting blocks may be used during such surgery to, for example, make several different cuts across the distal end of the femur and at least one cut across the proximal end of the tibia. Those of ordinary skill in the art will readily recognize that there exist many different types of these cutting blocks for use during many of the different widely performed primary and revision total knee procedures. However, other problems may exist in the knee joint, which require somewhat different procedures than that of typical total knee surgery.

Figure 1:
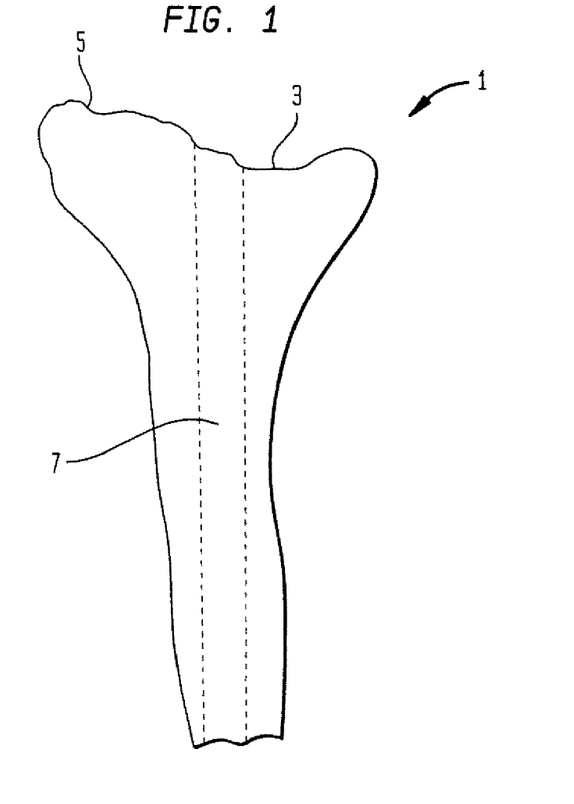
FIG. 1 is a front view of a right tibia with an unevenly worn medial side.

Often times, either prior or subsequent to an initial knee procedure, the bones of the knee joint will unevenly wear. For example, normal movement of the knee joint requires a relatively specific cooperation between the femur and the tibia. Over time, this cooperation, as well as the constant movement of the bones with respect to one another, will result in normal wear of the bones. However, due to injuries, defects or the like, sometimes, one or both of the distal end of the femur or the proximal end of the tibia will unevenly or unnaturally wear. Frequently, for example, the medial side of the proximal end of the tibia will develop a deeper than usual wear pattern with respect to its lateral side. FIG. 1 of the present application depicts a right tibia 1 exhibiting such a wear pattern 3. It is noted that such wear or degeneration of bone may also occur after an initial total knee surgery has been conducted.

In order to correct these types of defects, surgeons will often perform an augmentation surgery. Typically, this type of procedure entails resecting the entire proximal end of the tibia so that the remaining end exhibits one or more planar surfaces extending across the bone. This type of cut or resection necessarily requires that at least some lesser worn or unworn and otherwise healthy bone (shown in FIG. 1 as section 5 of tibia 1) be removed from the tibia. Thus, the overall bone material in the tibia is reduced, as well as material which may need to be removed in any additional revision surgeries performed on the knee. However, such material is typically replaced through the implantation of a tibial implant and augmentation block. Such surgery using augments is well known in the field.

Figure 7:
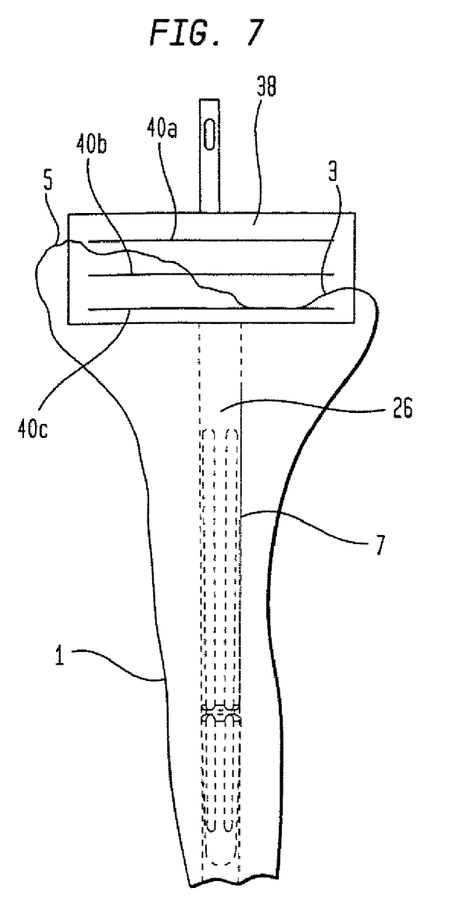
FIG. 7 is a front view of the tibia of FIG. 1 with a slotted cutting block attached thereto, optionally utilized for making a first cut.

Typically, a surgeon will utilize a single cutting block, like block 38 shown in FIG. 7, to make cuts on the proximal end of tibia at the different heights of the particular sections. In this regard, a surgeon will typically make a cut across the worn section 3 by utilizing a lower slot, and a cut across the lesser worn section 5 by utilizing one of the higher slots. However, performing such cuts often results in uneven or incorrectly gauged surfaces, which do not exactly match up with the tibial implant and augment to be implanted. For example, often times, the specific cutting slots on a given cutting block may not allow for the creation of cut surfaces that permit proper implantation of the tibial implant and augment. In many cases, this may require the use of additional or different cutting blocks, or may require a surgeon to perform free hand or otherwise approximated cuts.

Therefore, there exists a need for a cutting guide and method which allows for cut surfaces to be formed that are situated so as to permit proper implantation of an implant and augment during a surgery using augments.

BRIEF SUMMARY OF THE INVENTION

As used herein, when referring to bones or other parts of the body, the term "proximal" means closer to the heart and the term "distal" means more distant from the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

A first aspect of the present invention is a method of performing surgery on a tibia. The method preferably includes the steps of making a first cut across a first area of the tibia to create a first cut surface, the first cut being made by utilizing a first cutting guide, and making a second cut across a second area of the tibia to create a second cut surface, the second cut being made by utilizing a second cutting guide. Preferably, the first cut surface resides at a lower height or more distal level than that of the second cut surface so that a cutting surface of the second cutting guide and the second cut surface form a single substantially flat surface when the second cutting guide is placed adjacent to the first cut surface.

A second aspect of the present invention is a tibial augmentation guide. The guide preferably includes a guide portion having a tip surface and a bottom surface, the top and bottom surfaces being separated by a height. The guide preferably also includes a connection portion having an open end for cooperation with an intramedullary rod or the like. Preferably, the bottom surface or distal facing surface of the guide portion is adapted for engaging a substantially flat surface of a lower portion of a tibia that corresponds to a first cut surface and the top surface of the guide portion is adapted for guiding a cutting instrument to facilitate the creation of a second cut surface, the distance between the top and bottom surfaces of the guide portion being substantially equal to the distance between the top and bottom surfaces of an augment to be used.

A third aspect of the present invention is a surgical kit for use in performing tibial augmentation surgery. The kit preferably includes at least one guide, each guide including a guide portion having a top surface and a bottom surface, the top and bottom surfaces being separated by a height and a connection portion having an open end for cooperation with an intramedullary rod. The kit also preferably includes at least one intramedullary rod capable of engaging the connection portion of the at least one guide.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION

Figure 2:
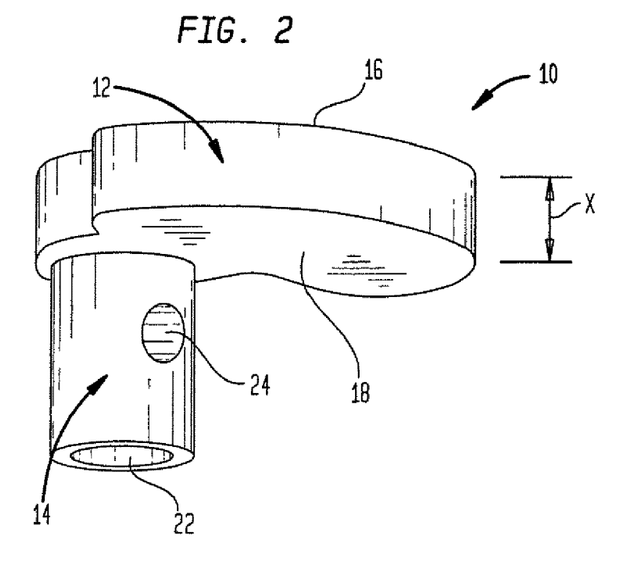
FIG. 2 is a front perspective view of a tibial augmentation guide according to one embodiment of the present invention.
Figure 3:
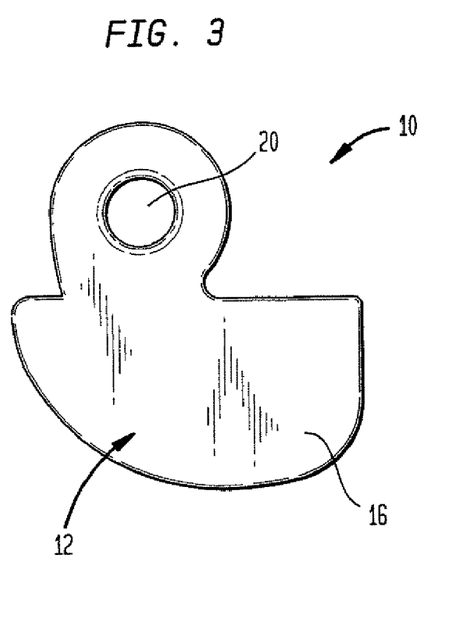
FIG. 3 is a top view of the tibial augmentation guide of FIG. 2.

Referring to the drawings, wherein like reference numerals refer to like elements, there is shown in FIGS. 2 and 3, a tibial augmentation guide designated generally by reference numeral 10. As best shown in FIG. 2, guide 10 preferably includes a guide portion 12 attached to a connection portion 14. In the preferred embodiment shown in the figures, guide portion 12 may further include a substantially flat top or proximal facing guide surface 16, a substantially flat bottom or distal facing bone engaging surface 18, and a threaded aperture 20 (best shown in FIG. 3). Surfaces 16 and 18 are preferably separated by a distance X, as shown in FIG. 2. On the other hand, connection portion 14 may further include an open end 22 and a connection aperture 24. In the preferred embodiment depicted in the figures, guide 10 is preferably constructed of stainless steel. However, in other embodiments, guide 10 may be constructed of many different biocompatible materials, such as titanium, cobalt chromes and certain polymers. It is noted that in embodiments in which guide 10 is constructed of a polymeric material, such may be relatively inexpensive to manufacture, and therefore could be intended to be disposable. However, this is clearly dependent upon the amount of costs associated in manufacturing the guide. In addition, as will be more fully set forth below, guide 10 is preferably shaped so as to fully cooperate with a previously resected proximal tibia portion. Nonetheless, those of ordinary skill in the art would recognize that the particular shape depicted in the figures could vary depending upon the particular size and/or shape of the tibia to be resected, or even with regard to different bones to be resected or the resection method to be utilized.

Figure 4:
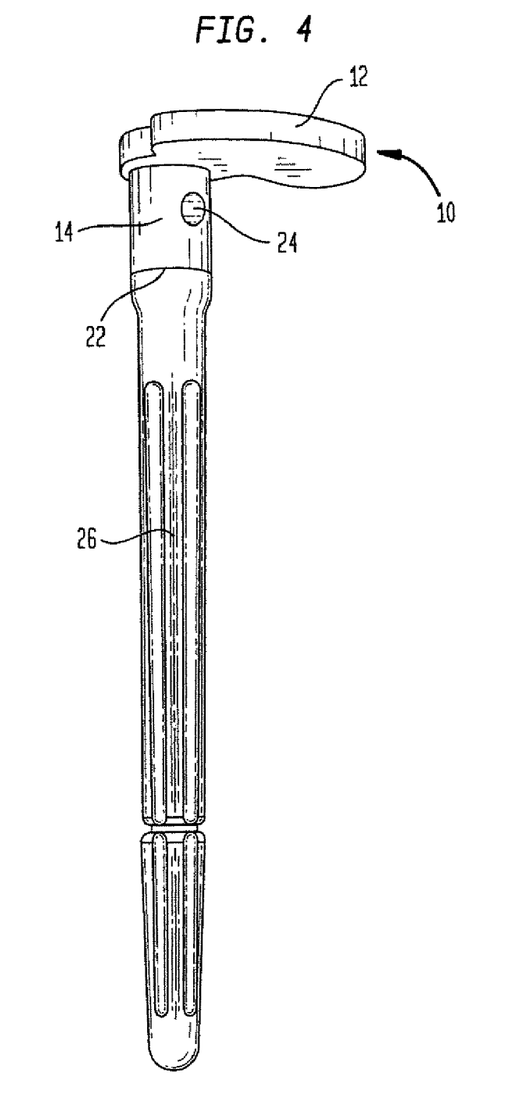
FIG. 4 is a front perspective view of a different thickness tibial augmentation guide with an intramedullary rod attached thereto.

FIG. 4 depicts guide 10, as illustrated in FIGS. 2 and 3, being connected to an intramedullary rod 26. It is noted that intramedullary rod 26 may be any well known type of intramedullary rod which is capable of being inserted into a reamed out intramedullary canal (designated by reference numeral 7 in FIG. 1) of a tibia or like bone. Such apparatus are well known to those of ordinary skill in the art. The connection between guide 10 and rod 26 may be of many different types. For example, rod 26 may include a threaded extension (not shown) which cooperates with a threaded open end 22 of connection portion 14. In a further example, rod 26 may include an extension (not shown) having a spring detent (not shown) thereon. In assembling such a latter design, the extension of rod 26 is preferably inserted in open end 22 of connection portion 14, until the spring detent of the rod engages aperture 24 of connection portion 14. This may allow for the easy assembly/disassembly of guide 10 to rod 14. In addition to the above described two examples of connections between guide 10 and rod 26, it is contemplated that many other well known connections may be utilized, such as retaining springs. It is also noted that rod 26 may be constructed of many different types of biocompatible materials, as are well known in the art. However, the material of rod 26 need not be the same as that of guide 10.

Figure 5:
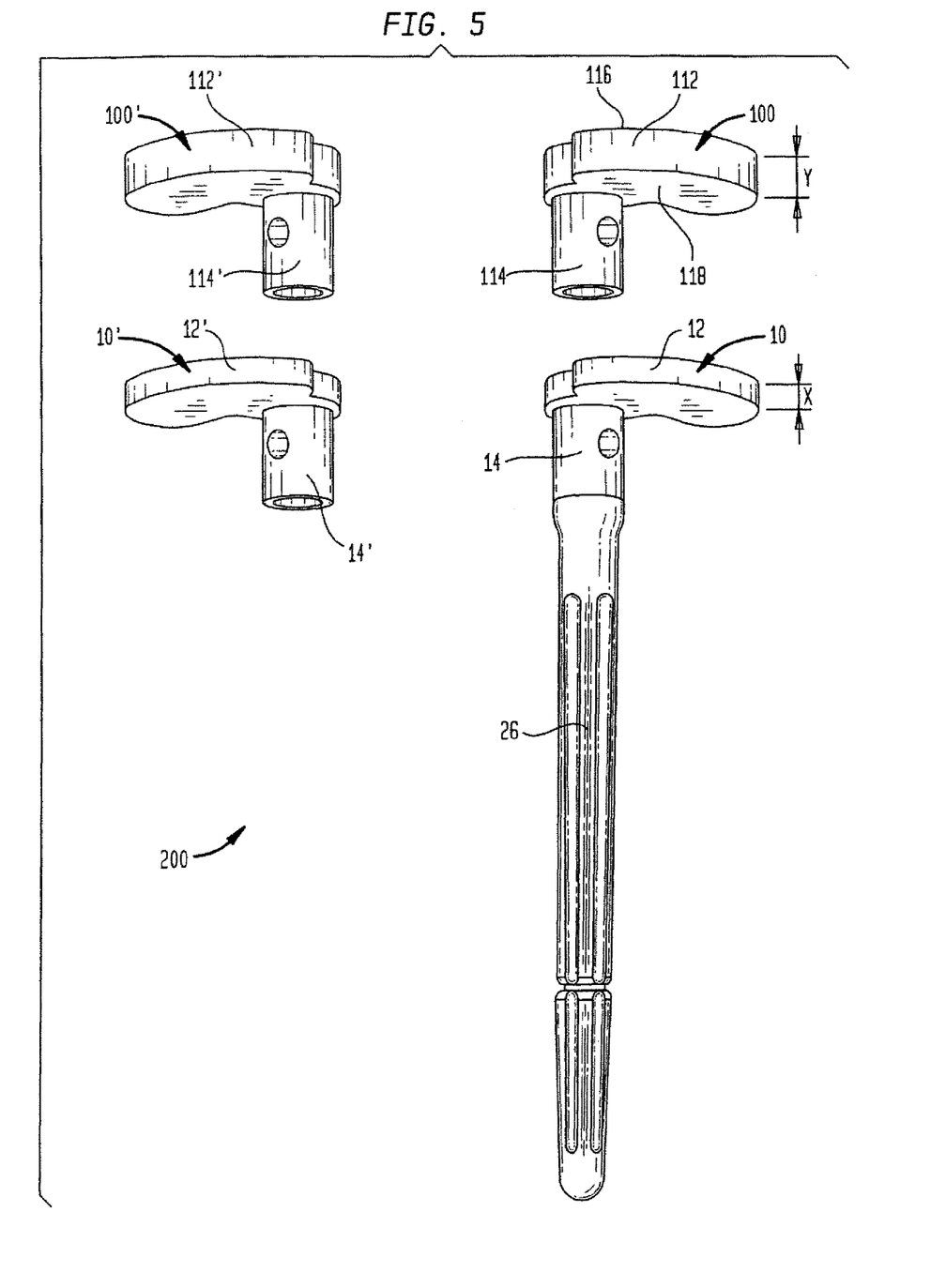
FIG. 5 is front perspective view of a kit in accordance with the present invention.

FIG. 5 depicts the guide 10 and intramedullary rod 26 combination of FIG. 4, as well as three additional guides 100, 10' and 100' similar to the above described guide 10. Like elements between the four guides 10, 100, 10' and 100' are identified with like references numerals, with those pertaining to guide 100 including numerals within the 100-series of numbers, those pertaining to guide 10' including numerals including the prime ("'") identifier, and those pertaining to guide 100' including numerals within the 100-series of numbers and having a prime identifier. Essentially, each of these elements makes up a kit 200 which may be provided to a surgeon performing a surgery using augments. Guide 100 is preferably identical to the above described guide 10, except that guide 100 includes a distance Y between its surfaces 116 and 118 that is thicker than the aforementioned distance X of guide 10. In other words, guide 100 is a thicker guide for use in connection with a tibia 1 which has a deeper wear pattern 3. This will be more fully discussed below. Guides 10' and 100' are likewise identical to guides 10 and 100, respectively, except that guides 10' and 100' are designed for use in oppositely oriented cuts. For example, if guides 10 and 100 are designed for cutting the lateral side of a right tibia, guides 10' and 100' are designed for cutting the lateral side of a left tibia. Thus, kit 200, as depicted in FIG. 5, would allow a surgeon to make two cuts at different levels, on both the left and right tibia. The above described detachable connectability of guide 10 with intramedullary rod 26 also applies to guides 100, 10' and 100', and therefore, the one rod 26 of kit 200 depicted in FIG. 5 is all that is needed to make the four different cuts. It is noted that kit 200 of FIG. 5 may be packaged in an easily sterilizable or autoclavable package, and/or may include additional objects. For example, the components depicted in FIG. 5 may be packaged along with tibial augment implants (like those discussed below) and/or instruments such as saws, drills or the like. In addition, although only two differently sized guides are depicted in FIG. 5, it is contemplated to provide more or less differently sized guides within a single kit 200, including guides of different thicknesses. It is also contemplated to provide an entirely disposable kit which may be initially sterilized and discarded subsequent to surgery. Finally, it should be understood that a single guide may be provided which could allow for resection of both lateral and medial sides of both the left and right tibia. Such a guide could be best understood as being of a universal design.

Figure 6:
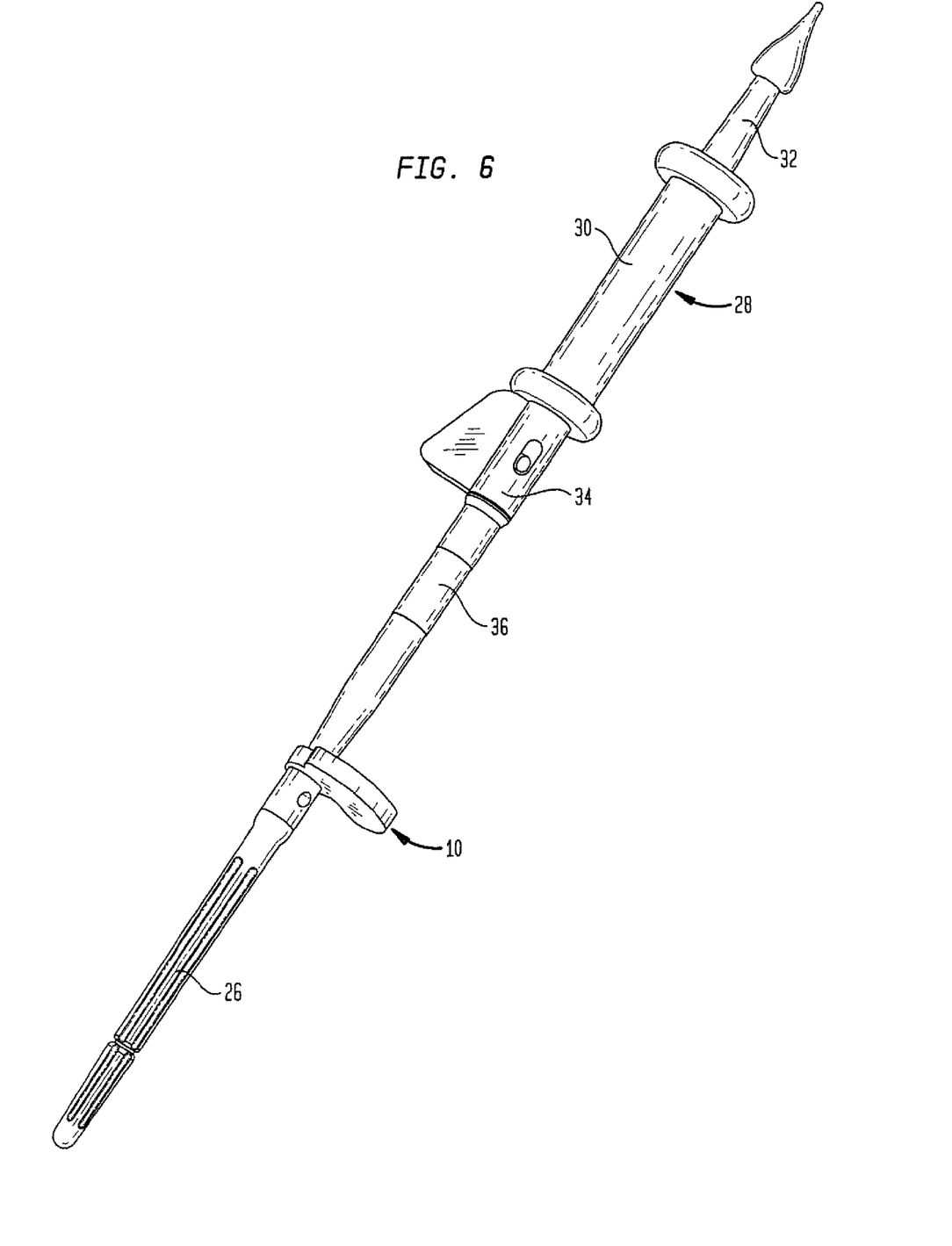
FIG. 6 is a front perspective view of the tibial augmentation guide and intramedullary rod of FIG. 4 with a slap hammer attached thereto.

A ready to be installed guide 10 is depicted in FIG. 6. More particularly, FIG. 6 illustrates guide 10 being connected to intramedullary rod 26, as well as to a slap hammer 28. It is noted that slap hammer 28 may be anyone of many well known devices suitable for translating force from a surgeon to a component being inserted in the body. For example, as best shown in FIG. 6, slap hammer 28 includes a handle 30 which is capable of sliding along an elongate portion 32 and contacting an end portion 34. In operation, a surgeon continuously slides handle 32 back and forth along portion 32, thereby continuously contacting or slapping end portion 34. This slapping force is translated to whatever is connected to slap hammer 28. In the embodiment depicted in FIG. 6, slap hammer 28 is connected at end portion 34 to a threaded rod 36. This threaded rod 36 is in turn connected to guide 10 at threaded aperture 20. Thus, operation of slap hammer 28 causes the force provided by a surgeon to be translated to guide 10 and intramedullary rod 26, thereby allowing the rod to become forcibly inserted in a reamed intramedullary canal, as will be discussed more fully below. It is noted that utilizing an instrument such as slap hammer 28 is only one method of ultimately inserting guide 10 and rod 26 into the tibia of a patient. Other well known methods may be utilized. In fact, it may be possible to directly contact top surface 16 of guide 10 with a hammer or the like.

A method of utilizing the above described guide 10 (as well as guides 100, 10' and 100') will now be described. Initially, subsequent to identifying a problem which requires a tibial augmentation, a surgeon will make an incision in the knee portion of a patient. Such an incision may be made in different areas of the knee, depending upon the particular method being utilized by the surgeon. For example, it is well known to make an initial incision anterior or directly in the front of the knee joint portion. Alternatively, it is also well known to make an incision on either the lateral or medial side of the knee and thereafter to perform the surgery from such an orientation, or to open the incision up to allow access to the anterior portion of the knee. Upon the making of the incision and opening a cavity suitable for working and inserting the necessary instruments and components through, the surgeon preferably reams the intramedullary canal 7 of tibia 1. Such is a well known process, and one which is frequently performed during a knee surgery. This reamed canal essentially provides for a fixed orientation point to which the various instruments utilized during the surgery can either be fixed to or oriented with respect to.

Figure 8:
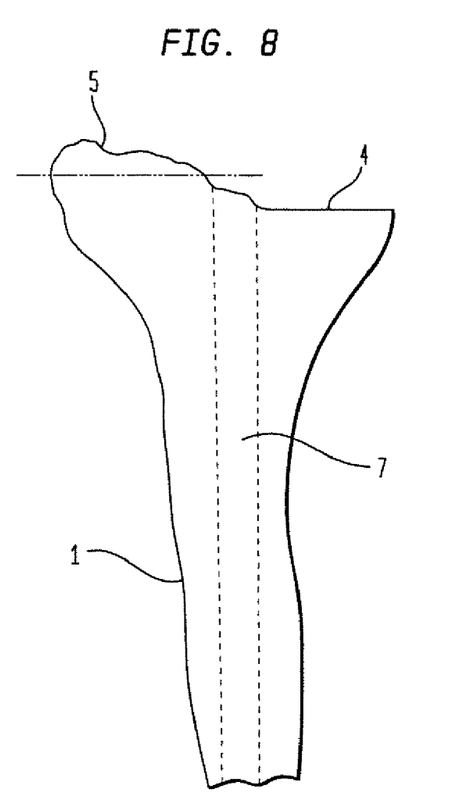
FIG. 8 is a front view of the tibia of FIG. 1 subsequent to cutting of a portion with the cutting block of FIG. 7.

As shown in FIG. 7, the first resection of tibia 1 is preferably done utilizing a slotted block or cutting guide 38. Such blocks, as discussed above, are well known in the art. It is noted that block 38 is preferably attached to an intramedullary rod (like that of the aforementioned rod 26) which is then inserted into the reamed out canal 7 of tibia 1. Alternatively, it is noted that block 38 may be pinned to tibia 1 or situated on an extramedullary assembly or the like. As shown in FIG. 7, block 38 may include a plurality of slots 40*a*, 40*b* and 40*c* for resecting at different levels. Thusly, depending upon the depth of wear pattern 3, the surgeon may utilize a different slot. In a preferred embodiment, a surgeon preferably then utilizes a saw or the like to resect straight across worn portion 3 of tibia 1. This provides a flat surface 4 which extends across tibia 1 at the lowest point of worn portion 3, as is best shown in FIG. 8. It is noted that non-worn or less worn lateral side 5 of tibia 1 is preferably not resected or at least minimally resected.

Figure 9:
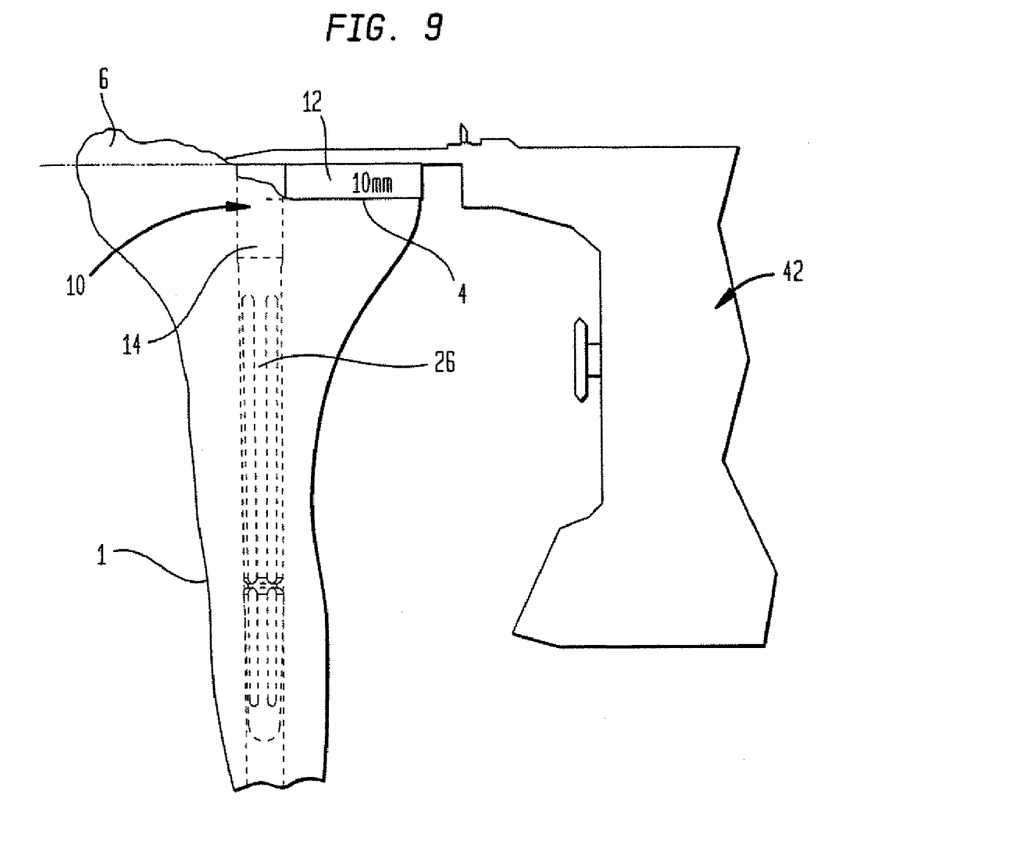
FIG. 9 is a front view of the tibia of FIG. 1 with the tibial augmentation guide and intramedullary of FIG. 4 attached thereto.
Figure 10:
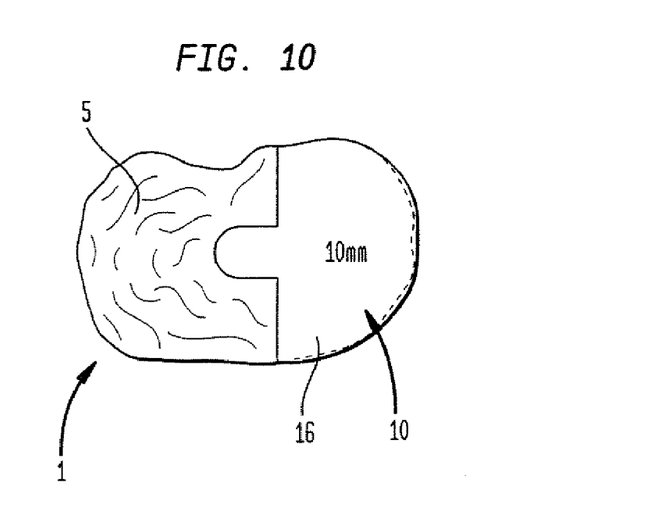
FIG. 10 is a top view of the tibia and tibial augmentation guide shown in FIG. 9.
Figure 11:
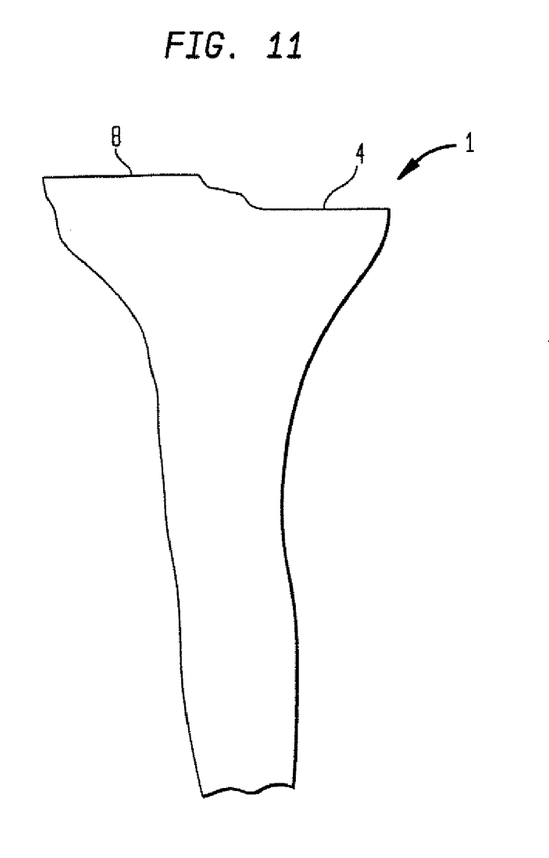
FIG. 11 is a front view of the tibia of FIG. 1 subsequent to first and second cut surfaces being formed.

With the worn portion 3 being resected, block 38 is then removed from rod 26 and guide 10 (or guide 100, 10' or 100') is preferably connected to rod 26. It is noted that rod 26 may be removed from the reamed intramedullary canal 7 of tibia 1 (e.g.—by operating the aforementioned slap hammer 28 in the opposite direction), or may remain therein during both the disconnection of block 28 and the connection of guide 10. This would be dictated by the above described connection means between rod 26 and the different guides/blocks. Once guide 10 is connected to rod 26 and placed adjacent to or touching tibia 1, as shown in FIG. 9, a saw (shown in FIG. 9 as element 42) or the like may be used to resect a small portion 6 of lateral side 5 of tibia 1. FIG. 10 depicts a top view of this cooperation between guide 10 and tibia 1. As is best shown in FIG. 11, this ultimately results in the formation of another flat surface 8, which resides at a greater height or a more proximal level than flat surface 4.

Figure 12:
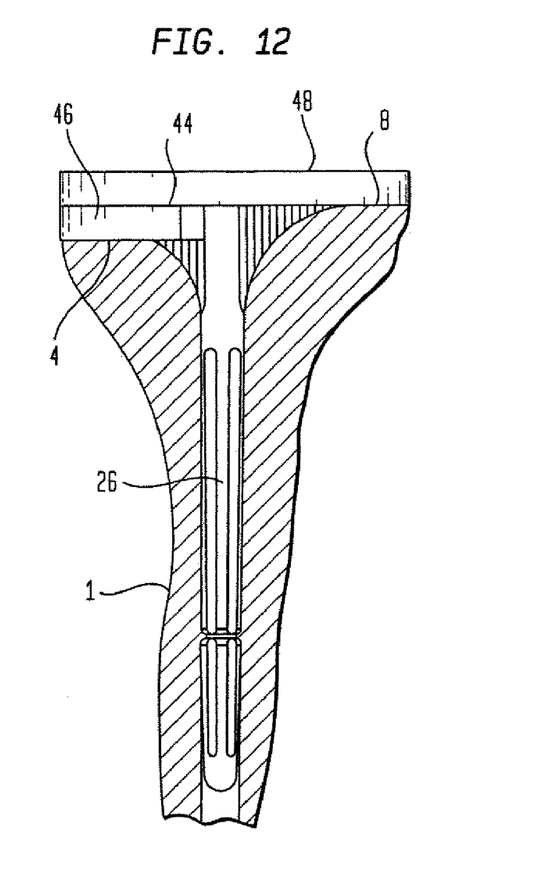
FIG. 12 is a front view of a right tibia with a tibial implant and an augmentation block attached thereto.

Referring to the final illustration depicted in FIG. 12, the surgeon preferably removes guide 10 from rod 26 subsequent to the creation of surface 8. Thereafter, a tibial implant 44 is preferably placed on the proximal portion of tibia 1. It is noted that implant 44 may be connected to intramedullary rod 26, which may or may not have remained in the reamed canal 7. Many different connections between rod 26 and implant 44 may be utilized. As shown in FIG. 12, an augmentation block 46 is also utilized in conjunction with implant 44 and preferably contacts surface 4 of tibia 1, which allows for a main portion 48 of implant 44 to contact both block 46 and surface 8 of tibia 1. Thus, implant 44 is designed to mate with the resected proximal end of tibia 1. It is noted that this cooperation allows for a significant amount of healthy bone to be retained on what was and remains lateral side 5 of tibia 1. Finally, a surgeon may then affix implant 44 to tibia 1. This may be accomplished by any well known fixation means, such as cement, bone screws or the like. Rod 26 may provide additional stability between implant 44 and tibia 1.

As is best shown in FIGS. 9 and 10, guide 10 is preferably designed so as to properly cooperate with tibia 1 and the remaining anatomy of the knee of a patient. Therefore, as was alluded to above, depending upon the orientation of the cut to made in the knee of a patient (e.g.—lateral side of the left vs. right tibia), different guide (10, 100, 10' or 100') may be required. This is due at least in part to the various ligament and tendons of the knee joint (not shown), as well as the particular landscape of the tibia itself. Depending upon the particular method of surgery (which may be dictated by the particular incision created by the surgeon), it may also be required to utilize a different guide. Those of ordinary skill in the art would readily recognize that guides 10, 100, 10' and 100' may be modified in order to properly mate with tibia 1, regardless of the surgical method employed or the particular anatomy of the patient. In addition, it to be understood to modify guide 10 of the present invention to include fewer, additional or different elements. For example, rather than having a top guide surface 16, it is possible to include a slotted top surface, not unlike guide 38 of FIG. 7. Of course, it is to be recognized that any slot of guide 10 would be required to allow a surgeon to cut away portion 6 of tibia 1.

Throughout, guides 10, 100, 10' and 100' have been described for use in conjunction with an overly worn medial side of tibia 1. However, it is to be understood that guides and methods of utilizing same may be provided for use in conjunction with an overly worn lateral side of tibia 1. Although such overly worn lateral sides are rarer than the same on the medial side of tibia 1, it is noted that guides 10, 100, 10' and 100' may be modified to allow resection in accordance with a lateral worn side.

Although the above described guides have been described in conjunction with a primary knee surgery, it is clearly contemplated to utilize such guides and methods of utilizing same in revision surgeries. In addition, it should be understood that the above described guides could be utilized in conjunction with similar surgery on other bones, such as the femur. Those of ordinary skill in the art would readily recognize how the particular guides and methods disclosed herein could be modified to be used in conjunction with surgery on such other bones. Finally, as mentioned above, kits in accordance with the present invention may be provided that include multiple guides, but it is also contemplated to provide a single universal guide which would allow multiple different cuts to be made. In any event, such guides could also be reusable or could be designed and manufactured so as to be disposable.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of performing surgery on a tibia comprising the steps of:
    making a first cut within a first plane across a first area of the outer surface of the tibia to create a first cut surface; and
    subsequent to making the first cut, making a second cut across a second area of the outer surface of the tibia and within a second plane substantially parallel to the first plane to create a second cut surface, the second cut being made by utilizing an augment cutting guide,
    wherein the first cut surface resides at a lower height than that of the second cut surface so that a cutting surface of the augment cutting guide and the second cut surface form a single substantially flat surface when the augment cutting guide is placed adjacent to the first cut surface.

2. Then method according to claim 1, wherein the first cut is made by utilizing a first cutting guide.

3. The method according to claim 1, further comprising the step of placing an implant adjacent both the first cut surface and the second cut surface.

4. The method according to claim 3, wherein the implant includes an augment block placed on the first cut surface.

5. The method according to claim 4, wherein the augment block has a thickness equal to the distance between the first and second cut surfaces.

6. The method according to claim 4, further comprising the step of placing a tibial prosthesis onto the single substantially flat surface formed by the augment block and the second cut surface.

7. The method according to claim 1, wherein said cutting steps are performed with a surgical saw.

8. The method according to claim 2, wherein the first cutting guide includes at least one cutting slot.

9. The method according to claim 2, further comprising the step of preparing an intramedullary canal of the tibia.

10. The method according to claim 9, further comprising the step of inserting an intramedullary rod in the prepared intramedullary canal of the tibia.

11. The method according to claim 10, wherein the intramedullary rod is capable of cooperating with the first cutting guide and the augment cutting guide.

12. The method according to claim 11, further comprising the steps of connecting the augment cutting guide to an intramedullary rod and inserting the intramedullary rod into the prepared intramedullary canal.

13. A method of performing surgery comprising the steps of:
    making a first cut within a first plane across a first area of an articulating surface of a bone to create a first cut surface;
    providing a first cutting guide having an upper surface and a lower surface separated by a first thickness;
    placing the first cutting guide on the bone so that the lower surface contacts the first cut surface; and
    using the upper surface of the cutting guide to make a second cut across a second area of the articulating surface of the bone and within a second plane substantially parallel to the first plane to create a second cut surface,
    wherein the first cut surface resides at a lower height than that of the second cut surface so that the upper and second cut surfaces form a single substantially flat surface when the lower surface contacts the first cut surface.

14. The method according to claim 13, wherein the first cutting guide is a unitary body.

15. The method according to claim 13, further comprising the steps of preparing an interior canal of the bone and inserting a rod connected to the first cutting guide into the prepared canal.

16. The method according to claim 15, further comprising the step of connecting the first cutting guide to the rod.

17. The method according to claim 13, further comprising the step of selecting the first cutting guide from a plurality of cutting guides.

18. A method of preparing a tibia comprising the steps of:
    making a first cut within a first plane across a first area of an outer surface of the tibia to create a first cut surface;
    selecting a first cutting guide from a plurality of cutting guides, the first cutting guide having an upper surface and a lower surface separate by a first thickness;
    positioning the first cutting guide so that the lower surface of the first cutting guide contacts the first cut surface;
    using the upper surface of the cutting guide to make a second cut across a second area of the outer surface of the tibia within a second plane substantially parallel to the first plane to create a second cut surface,
    wherein the first cut surface resides at a lower height than that of the second cut surface so that the upper and second cut surfaces form a single substantially flat surface when the lower surface contacts the first cut surface.

19. The method according to claim 18, wherein the plurality of cutting guides include different thicknesses.

20. The method according to claim 18, wherein the second cut surface is created utilizing a cutting tool oriented from a medial or lateral aspect of the tibia.

* * * * *